(12) United States Patent
Cavanaugh et al.

(10) Patent No.: US 7,433,042 B1
(45) Date of Patent: *Oct. 7, 2008

(54) SPATIALLY CORRECTED FULL-CUBED HYPERSPECTRAL IMAGER

(75) Inventors: David B. Cavanaugh, San Diego, CA (US); Mark Dombrowski, Escondido, CA (US); Brian Catanzaro, San Diego, CA (US)

(73) Assignee: Surface Optics Corporation, San Diego, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/774,599

(22) Filed: Jul. 7, 2007

Related U.S. Application Data (63) Continuation-in-part of application No. 10/984,561, filed on Nov. 9, 2004, now Pat. No. 7,242,478.

(60) Provisional application No. 60/527,252, filed on Dec. 5, 2003.

(51) Int. Cl.
  *G01N 21/25* (2006.01)
(52) U.S. Cl. .................................. 356/419
(58) Field of Classification Search ................ 356/419; 250/339.07
  See application file for complete search history.

(56) References Cited

U.S. PATENT DOCUMENTS

| | | | | |
|---|---|---|---|---|
| 5,166,755 A | * | 11/1992 | Gat | 356/419 |
| 5,504,575 A | * | 4/1996 | Stafford | 356/330 |
| 5,729,011 A | * | 3/1998 | Sekiguchi | 250/226 |
| 5,926,283 A | * | 7/1999 | Hopkins | 356/419 |
| 6,031,619 A | * | 2/2000 | Wilkens et al. | 356/419 |
| 6,097,023 A | * | 8/2000 | Schofield et al. | 250/208.1 |
| 6,222,631 B1 | * | 4/2001 | Terauchi | 356/419 |
| 6,396,053 B1 | * | 5/2002 | Yokoi | 250/234 |
| 6,660,988 B2 | * | 12/2003 | Lee et al. | 250/208.1 |
| 6,678,048 B1 | * | 1/2004 | Rienstra et al. | 356/419 |
| 6,765,617 B1 | * | 7/2004 | Tangen et al. | 348/340 |
| 6,868,231 B2 | * | 3/2005 | Irving et al. | 396/322 |
| 7,227,116 B2 | * | 6/2007 | Gleckler | 250/208.1 |
| 7,227,459 B2 | * | 6/2007 | Bos et al. | 340/461 |
| 7,280,205 B2 | * | 10/2007 | Bouzid et al. | 356/326 |
| 2002/0175286 A1 | * | 11/2002 | Murguia | 250/339.07 |
| 2007/0081815 A1 | * | 4/2007 | Zomet et al. | 396/327 |
| 2007/0097249 A1 | * | 5/2007 | Korenaga | 348/335 |
| 2007/0188735 A1 | * | 8/2007 | Braunecker et al. | 356/4.09 |
| 2008/0029708 A1 | * | 2/2008 | Olsen et al. | 250/372 |
| 2008/0029714 A1 | * | 2/2008 | Olsen et al. | 250/475.2 |
| 2008/0030597 A1 | * | 2/2008 | Olsen et al. | 348/227.1 |

* cited by examiner

*Primary Examiner*—Michael A. Lyons
*Assistant Examiner*—Scott M Richey
(74) *Attorney, Agent, or Firm*—MIchael W. Landry (57) ABSTRACT

A hyperspectral imager that achieves accurate spectral and spatial resolution by using a micro-lens array as a series of field lenses, with each lens distributing a point in the image scene received through an objective lens across an area of a detector array forming a hyperspectral detector super-pixel. Spectral filtering is performed by a spectral filter array positioned at the objective lens so that each sub-pixel within a super-pixel receives light that has been filtered by a bandpass or other type filter and is responsive to a different band of the image spectrum. The micro-lens spatially corrects the focused image point to project the same image scene point onto all sub-pixels within a super-pixel.

5 Claims, 12 Drawing Sheets

| 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|
| 5 | 6 | 7 | 8 | 5 | 6 | 7 | 8 | 5 | 6 | 7 | 8 | 5 | 6 | 7 | 8 |
| 9 | 10| 11| 12| 9 | 10| 11| 12| 9 | 10| 11| 12| 9 | 10| 11| 12|
| 13| 14| 15| 16| 13| 14| 15| 16| 13| 14| 15| 16| 13| 14| 15| 16|
| 1 | 2 | 3 | 4 | 1 | 2 | 3 | 4 | | | | | | | | |
| 5 | 6 | 7 | 8 | 5 | 6 | 7 | 8 | | | | | | | | |
| 9 | 10| 11| 12| 9 | 10| 11| 12| | | | | | | | |
| 13| 14| 15| 16| 13| 14| 15| 16| | | | | | | | |

SPATIALLY CORRECTED FULL-CUBED HYPERSPECTRAL IMAGER

RELATED APPLICATIONS

This application is a continuation-in-part of application Ser. No. 10/984,561 filed Nov. 9, 2004, with a projected issue date of Jul. 10, 2007 as U.S. Pat. No. 7,242,478, which claims priority to U.S. provisional patent application No. 60/527,252 filed Dec. 5, 2003 entitled "Spatially corrected full-cubed Hyperspectral imager", incorporated herein by reference.

BACKGROUND

1. Field of the Invention

The invention relates generally to spectrometry and particularly to hyperspectral imaging.

2. Prior Art

Hyperspectral imagers (HSI) are a class of spectrometers that record energy in many discrete spectral bands or colors simultaneously at a multitude of spatial picture elements, called pixels. Standard broadband imagers record one value at each picture element for all the detected incident energy across a wide spectrum. Hyperspectral imagers differ from standard broadband imagers by creating an additional spectral dimension in addition to the two spatial dimensions created from a two-dimensional array of detectors. Each HSI picture element may have ten to hundreds of wavelength values recorded.

Some hyperspectral imagers use a scanning approach where a scan mirror scans an image across the entrance slit of a spectrometer (pushbroom), often employing a prism or grating to disperse the various wavelengths across a detector array. Scanning hyperspectral imagers are complex and large. Such imaging spectrometers are often mounted on aircraft without a scan mirror; in such cases, the motion of the aircraft serves to scan the scene.

A class of imagers known as multispectral imagers or multispectral cameras resolve many frequencies of the image into a limited number of bands, providing a coarse measure of energy as a function of frequency. These systems use a color-sorting prism to separate the image into three spectral bands. Each prism output can drive a monochrome imaging array or a color image array. An example of this type of multispectral camera is available from Redlake MASD, Inc. (formerly DuncanTech), which has a camera configured with a 3-way color-sorting prism illuminating two monochrome imagers and one 3-color imager to cover a total of five spectral bands. The color sorting or separating prism provides bandpass filtering of the image into sub-bands. Trim filters in front of each image array can be used to provide additional wavelength selectivity and rejection of out of band energy.

Once approach to achieve multispectral capability with a single imaging array, such as a complimentary metal oxide semiconductor (CMOS) or charged-coupled device (CCD) array, uses a color filter array (CFA) to limit the color band passing through to each pixel. The wide spectral response of a pixel is limited to the spectral band of the corresponding CFA element applied to that pixel. This technique is common in color video cameras and digital still cameras, using a Bayer filter pattern of interleaved red, blue, and green filters. An interpolation or de-mosaicing algorithm is used to reconstruct a color corrected image of uniform pixels from a mosaic of separate color pixels created by the filter pattern. These algorithms use a weighted combination of pixel values with neighboring pixel values. This approach creates an approximation of the hyperspectral information. Each pixel detects a different color from a slightly different position in the image scene. In a conventional pushbroom scanning system, each wavelength associated with a single spatial pixel in the cube views the exact same region of the scene. In a typical Bayer filter approach, each pixel views a slightly different region of the scene. Mathematical operations performed by image processing cannot reconstruct information lost as a result of the Bayer filter design. The de-mosaicing process produces an aesthetically acceptable result for some consumer applications. However, this loss of data can affect a variety of applications including those where a direct spectral comparison of spatially correlated images is required.

Imaging arrays fabricated with integrated circuit semiconductor technology have active and inactive areas. In addition to the light sensitive detector areas, other circuitry used for readout of the detector pixels uses area in the focal plane but does not collect light. This ratio of light sensitive and light insensitive areas is referred to as fill factor. Various technologies have different fill factors. In order to improve light sensitivity, micro-lens arrays (MLA) have been widely used in both CMOS and CCD arrays to increase the proportion of light that is directed to the light sensitive areas. In prior art designs, there is a one-to-one correspondence between a lens in the MLA and a pixel in the detector array.

A color filter array allows using a single detector array to resolve more than one color, but reconstructing the image formed from the interleaved filter array impairs accuracy for high precision hyperspectral imaging.

SUMMARY OF THE INVENTION

A spatially corrected hyperspectral imager according to the present invention achieves accurate spectral and spatial resolution by using a micro-lens array (MLA) as a series of field lenses, with each lens distributing a point in the image scene received through an objective lens across an area of a detector array, also called a focal plane array (FPA), forming a hyperspectral detector super-pixel. Each sub-pixel within a super-pixel receives light that has passed through a filter used to spectrally characterize the object. The micro-lens spatially corrects the focused image point to project the same image scene point onto all sub-pixels within a super-pixel.

The array of micro-lens is positioned between the objective lens and the detector array to distribute light for a super-pixel to all of its sub-pixels. One lens of the micro-lens array corresponds to one super-pixel of the detector array. A super-pixel consists of several sub-pixels. Each sub-pixel within a super-pixel collects energy at different wavelengths by use of a color filter array in the optical path between the MLA and the detector array. Since each sub-pixel in any given super-pixel views the same portion of the image, the errors in conventional Bayer image sensors and de-mosiacing algorithms are no longer a limitation. In the most straightforward application, a super-pixel consists of an array of sub-pixels within the detector array where each sub-pixel receives light from a unique narrow-band filter and is thus responsive to a unique band of wavelengths. The color filter matrix pattern, for example, employing 16 unique narrow-band filters in a 4×4 array, is repeated across the entire detector array. In this example, a super-pixel consisting of 16 sub-pixels represents one point in the image and measures 16 different wavelengths.

A conventional MLA with one lens per sub-pixel may be used for increasing fill factor, which may be an integral part of the detector array. The super-pixel MLA is an entirely separate element used in addition to the MLA that may be used for increasing fill factor.

A color filter array of various discrete bandpass filters forms a filter matrix. The bandpass filters can cover a contiguous range of wavelengths or non-contiguous wavelengths. The filters in the array may be narrow band, broad band, or complex in spectral response.

Each lens of the micro-lens array covers one super-pixel. Each super-pixel is an array of individual sub-pixels and forms a multiband detector. The array of multiband detectors forms a two-dimensional imager with a third spectral dimension, resulting in a full-cubed hyperspectral imager.

The super-pixel MLA may be used with a sensor that includes a fill factor improving MLA. If it is, then an additional MLA is required to preserve the field of view of the super-pixel.

In another embodiment of the invention, which further increases the number of colors resolved by the hyperspectral imager, a color separator is used to split the full band being imaged into sub-bands. Each sub-band is then imaged with one hyperspectral imaging array. For example, a 3-way color separator projecting the three sub-bands onto three hyperspectral imagers, using detector arrays with super-pixels capable of detecting 16 colors, will achieve 48-color resolution.

In one particular embodiment of the invention, the color separator uses three-color separating prisms to direct three broad spectral bands to three CMOS imagers located on the output faces of each prism. Two dichroic filters located at the prism interfaces act as band splitters. The dichroic filters can be deposited directly on the surface of the prisms. Other methods of color separation are well known, including layered cubes, layered filters, 45 deg dichroic mirrors, and gratings.

In one embodiment of the invention, the optical design incorporates a single array of spectrally selective optical filters into the lens of the imaging system. The filter array is placed at the entrance pupil of the objective lens system. An array of micro-lenses forms replicate images of the array of filters across the focal plane. All light that reaches the detector focal plane passes through one of the filter elements in the array and the light passing through one filter element is focused onto one detector pixel.

DETAILED DESCRIPTION

Figure 1:
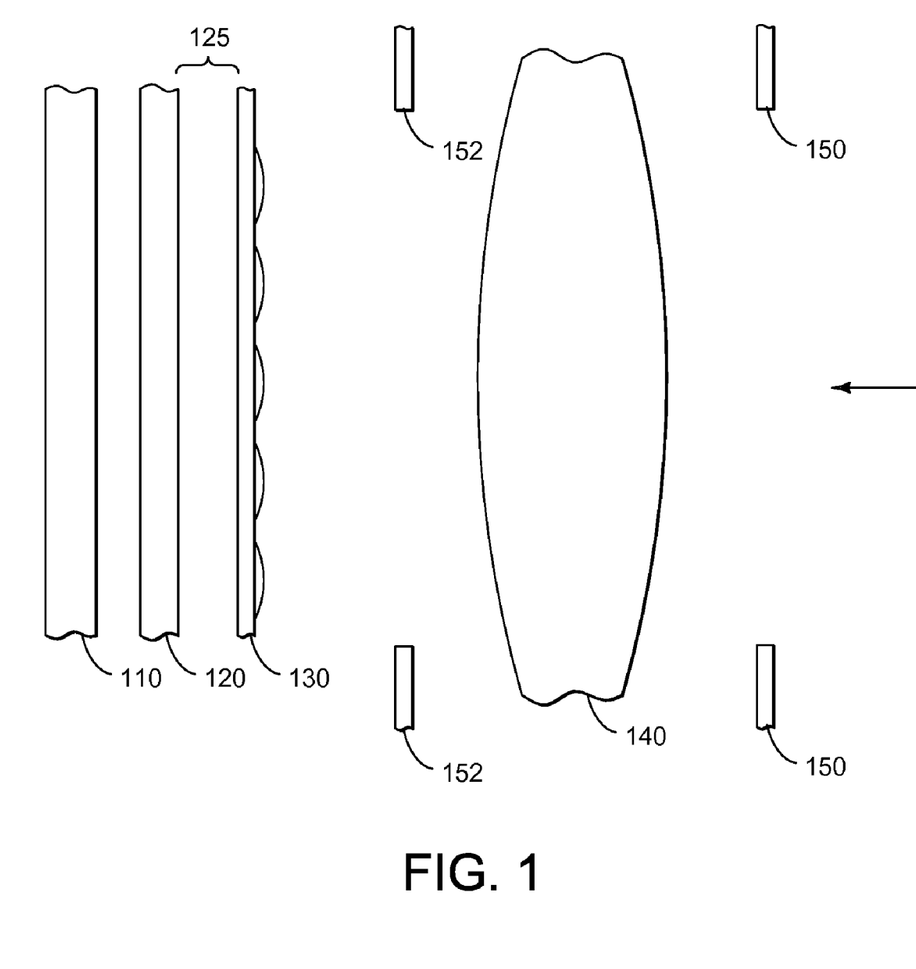
FIG. 1 shows an image sensor, filter mask, micro-lens, and objective lens according to the present invention.

FIG. 1 shows the side view of the layers of the hyperspectral imager according to the present invention. Detector array 110, color filter array 120, and micro-lens array (MLA) 130, each shown separated for clarity, are rigidly attached to each other. MLA 130 is positioned where objective lens 140 forms an image of the object under observation. Detector 110 is placed where the lenses in MLA 130 form an image of the exit pupil of objective lens 140. Color filter array 120 should be placed as close as feasible to detector 110 to ensure minimal spectral crosstalk and maximum efficiency. Optional spacing 125 can be filled with glass, other optically transparent material, vacuum, or air. Each lens of MLA 130 distributes light across a super pixel area of filter array 120 and detector array 110.

Objective lens 140 is preferably a telecentric lens. The chief ray for each field point of the image formed by a telecentric lens is perpendicular to the image plane. The chief ray is the ray for each field point (angle) that passes through the center of the aperture stop in the optical system. Alternatively, another field lens can be placed at or near the image plane to direct the light into the MLA as a telecentric lens would, thus causing a non-telecentric lens to function as a telecentric lens.

Aperture 150 represents the entrance pupil of the optical system and aperture 152 represents the exit pupil of the optical system. These pupils are images of the aperture stop, the aperture that limits the axial cone of energy from the object. The entrance 150 and exit 152 pupils may be actual objects or merely images of the aperture stop. To maximize light throughput and minimize crosstalk from adjacent super-pixels, the shape of the exit pupil 150 should match the shape (outline) of the layout of the detector pixels used to form the super-pixel. The focal length of MLA 130 should be designed to produce a demagnified image of exit pupil 152 that matches the layout of the detector pixels. For lenses whose aperture stop shape does not match the shape of the layout of the detectors (e.g. square, rectangular, hexagonal, or circular), a stop can be placed at the location of aperture 150 or 152 to change the effective shape of the aperture stop.

Each lens in the MLA images the exit pupil of the optics path, which has the effect of imaging the limiting aperture, onto the detector array. The image is out of focus at each detector sub-pixel because the MLA is at the focus of the objective lens, however, at the super-pixel level the scene is in focus. While not necessary for the invention to operate, forming the limiting aperture shape to match the shape of the super-pixel allows optimum performance.

Figure 2:
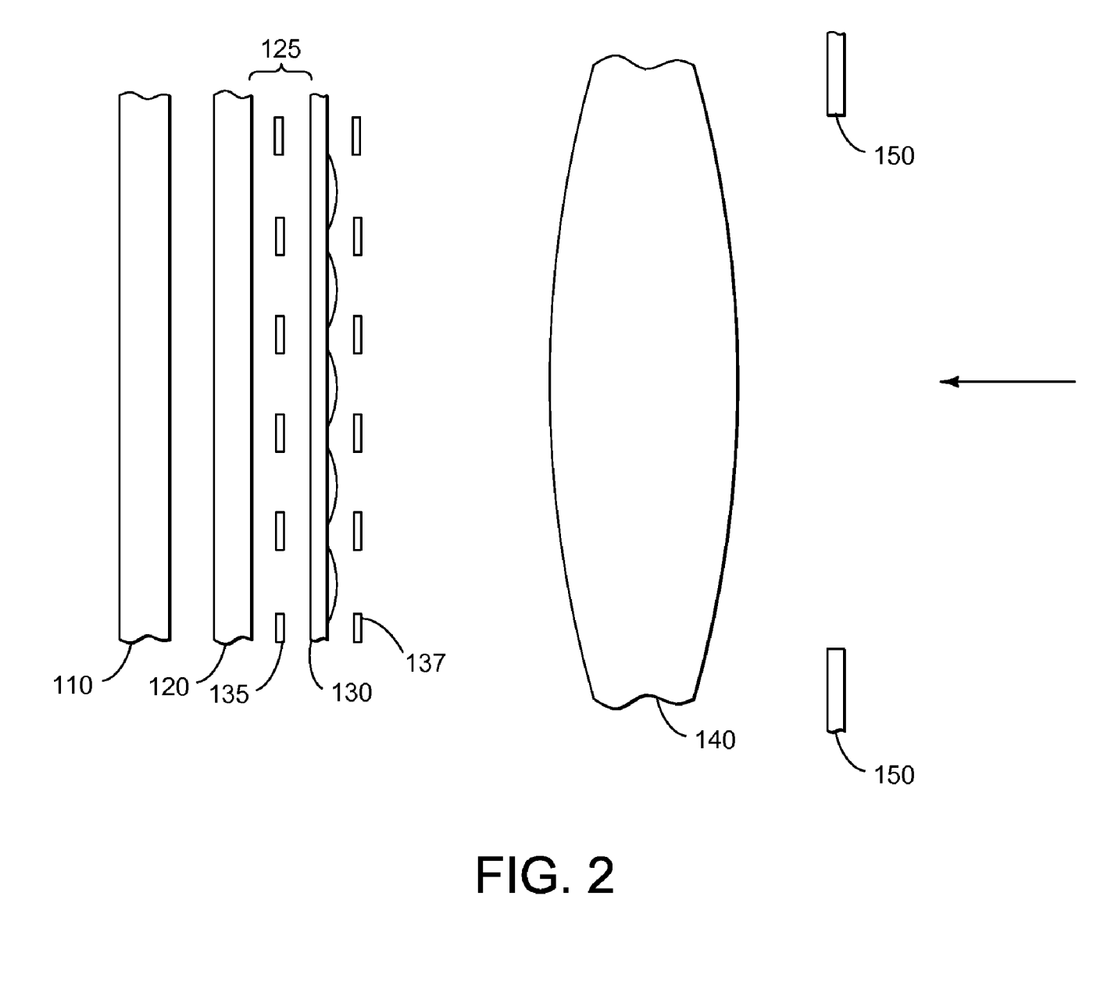
FIG. 2 shows an image sensor with a mask array near the micro-lens array.

FIG. 2 shows an alternative approach to achieving energy separation by using an aperture mask positioned in front the MLA or in front of the color filter. The aperture mask has an array of openings that restrict light to an area that is the shape of the super-pixel. Aperture masks 135 and 137 are shown in two alternative positions to act as a field stop. Aperture masks 135 and 137 can be constructed at tubular baffles.

Figure 3:
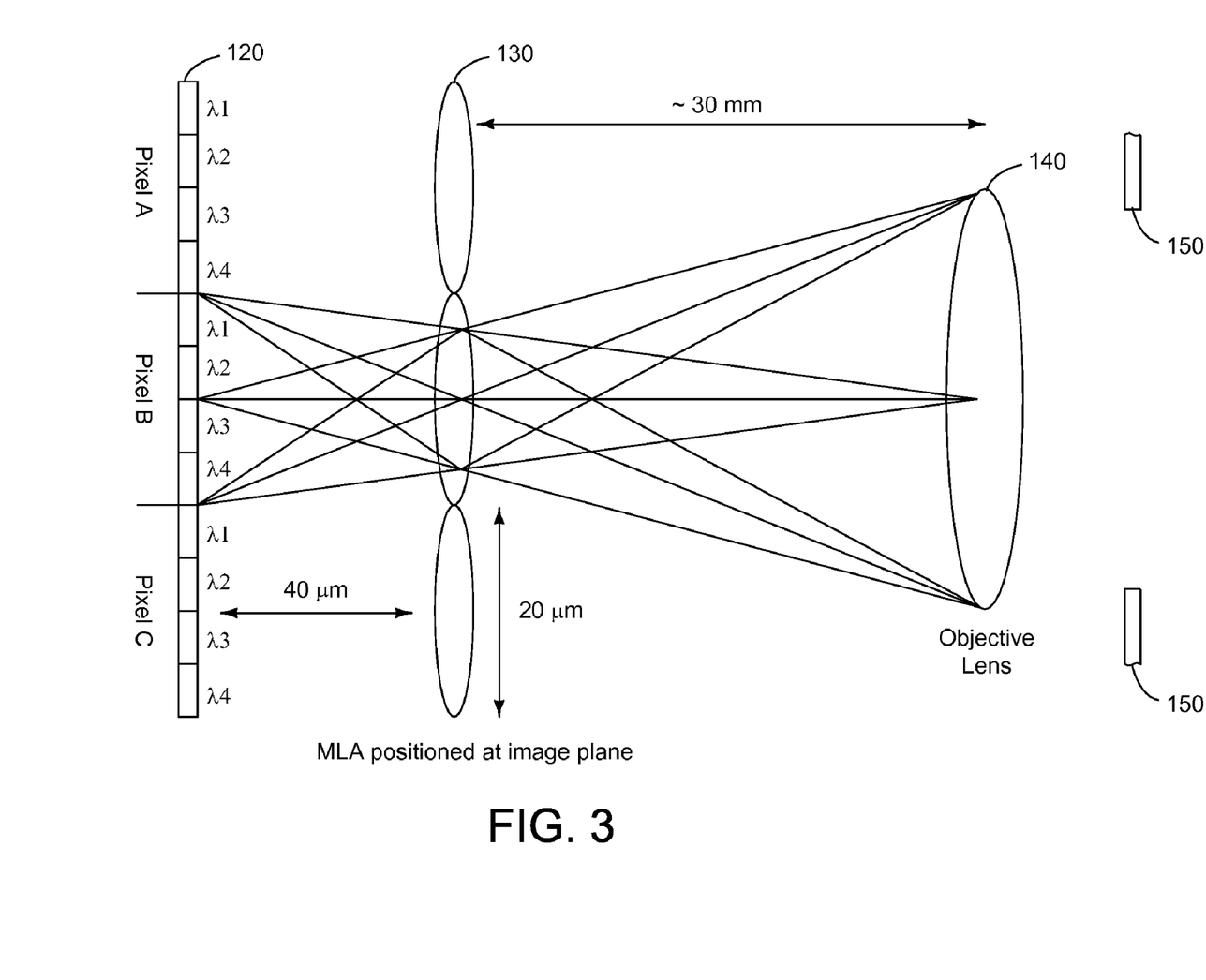
FIG. 3 shows a micro-lens array positioned between an objective lens and a filter mask with a representative ray path.

FIG. 3 shows ray tracing of the optical path for one super-pixel. Pixel A, Pixel B, and Pixel C represent super-pixels composed of an array of sub-pixels, for example a 4×4 array in this illustration. Color filter array 120 is used to create different wavelength responses in each of the sub-pixels within each super-pixel. Micro-lens array 130 is used as an array of field lenses with each lens corresponding to a super-pixel. Limiting aperture 150 defines the shape of the light incident on filter array 120.

A complete hyperspectral detector array, for example, uses a color filter array with a repeating matrix of 4×4 narrow band filters with 10 nm bandwidth in conjunction with a 1936× 1086 detector array produces a spatial resolution of 484×271 points with 16-wavelength detection at 10 nm spectral resolution. A suitable CMOS array is available from Rockwell Scientific, which has intrinsic response from less than 400 nm to greater than 1000 nm.

Micro-Lens Array

Figure 4:
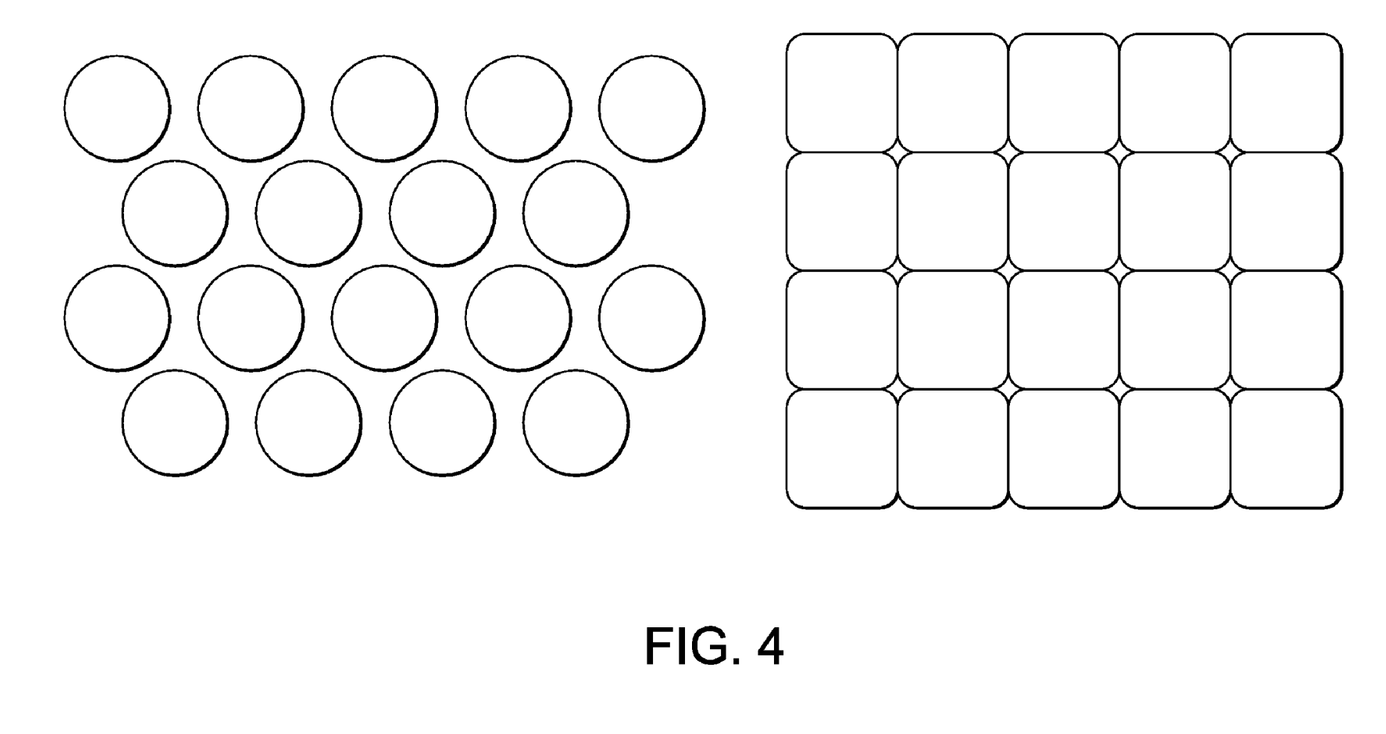
FIG. 4 shows examples of a segment of a micro-lens array with a hexagonal and square packing.

FIG. 4 shows two examples of micro-lens array packing techniques. Circular lenses can be arranged in a staggered pattern. The lenses can touch or have a gap between each lens. Square lenses can be arranged in a regular pattern as shown or have a slight stagger (not shown) to allow denser packing that fills the space at the corners. Lenses can alternatively be rectangular shaped. Regardless of the shape of the MLA lens, a single micro lens spreads the light incident onto the lens across the area of a super-pixel. The MLA aperture should roughly match the super-pixel shape and the shape of the aperture stop. Deviations from this will cause light loss.

The micro lens is placed at the image formed by the objective lens and each micro lens functions as a field lens. Such a field lens in the optical path reduces the divergence spread of the light rays, making the light more collimated, thus the position of the optics behind the image plane is less critical. The direction of each cone of light projected from the objective lens is changed so that the cone is bent toward the centerline. Light focused to a point at the micro lens is spread across the super-pixel area. An image formed at the focus of the objective lens is refocused at the super-pixel resolution instead of diffraction-limited resolution of the objective.

Each lens has an effective collection aperture and the light received at any point in the aperture is distributed evenly across the underlying super-pixel.

The pitch of the micro-lenses is adapted to the size of the super-pixel. For example, with pixels of 5 um square forming a super-pixel of 20 um square, the center-to-center spacing of each micro-lens would be 20 um.

Micro-lenses are described generally and manufacturing techniques are disclosed in the following references, each is incorporated herein by reference:

Nakama et al., U.S. Pat. No. 5,867,321, "Planar microlens array and method of making same"; Li, U.S. Pat. No. 6,587,147, "Microlens array"; Teshima et al., U.S. Pat. No. 6,506,623, "Microstructure array, mold for forming a microstructure array, and method of fabricating the same"; Hamanaka et al., U.S. Pat. No. 6,432,328, "Method for forming planar microlens and microlens obtained thereby"; Border et al., U.S. Pat. No. 6,402,996, "Method of manufacturing a microlens and a microlens array"; Tijima, U.S. Pat. No. 6,374,024, "Image sensor and method of manufacturing the same"; Marchant et al., U.S. Pat. No. 6,353,502, "Vcsel field construction"; Assadi et al., U.S. Pat. No. 6,540,946, "Microlens for surface mount products".

Filter Matrix

Figure 5:
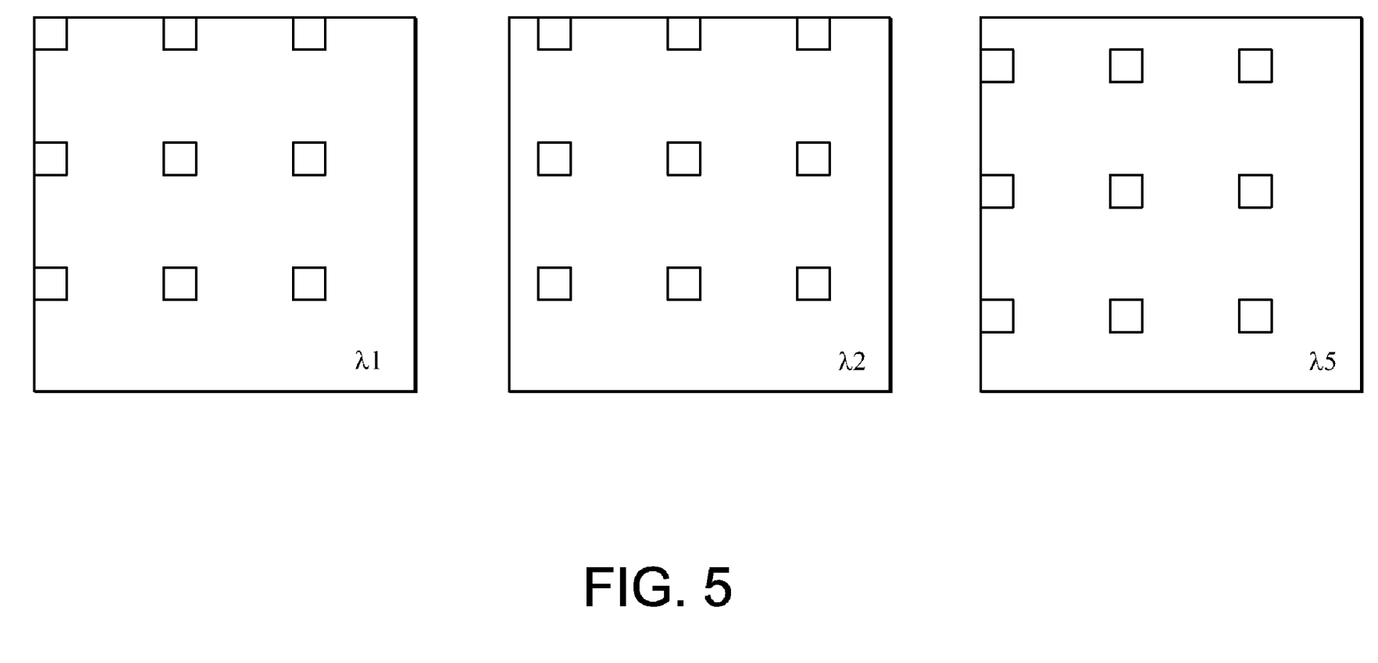
FIG. 5 shows example of photomasks for fabricating a filter matrix for use with the present invention.

FIG. 5 shows three masks in a series of masks used to construct the filter matrix. A 4×4 filter matrix requires a series of 16 masks; each mask has openings, represented by the small square regions, corresponding to one of the pixel positions at each super-pixel. Photolithography techniques are used to construct the masks and deposit the wavelength-determining coatings at each pixel position. The process of creating masks and depositing coating for bandpass filters is well known. Pixel sizes of 5×5 um and smaller are well within the state of the art in photolithography. In addition to non-overlapping mask, absorptive Filters may be made in an overlapping fashion.

Figure 6:
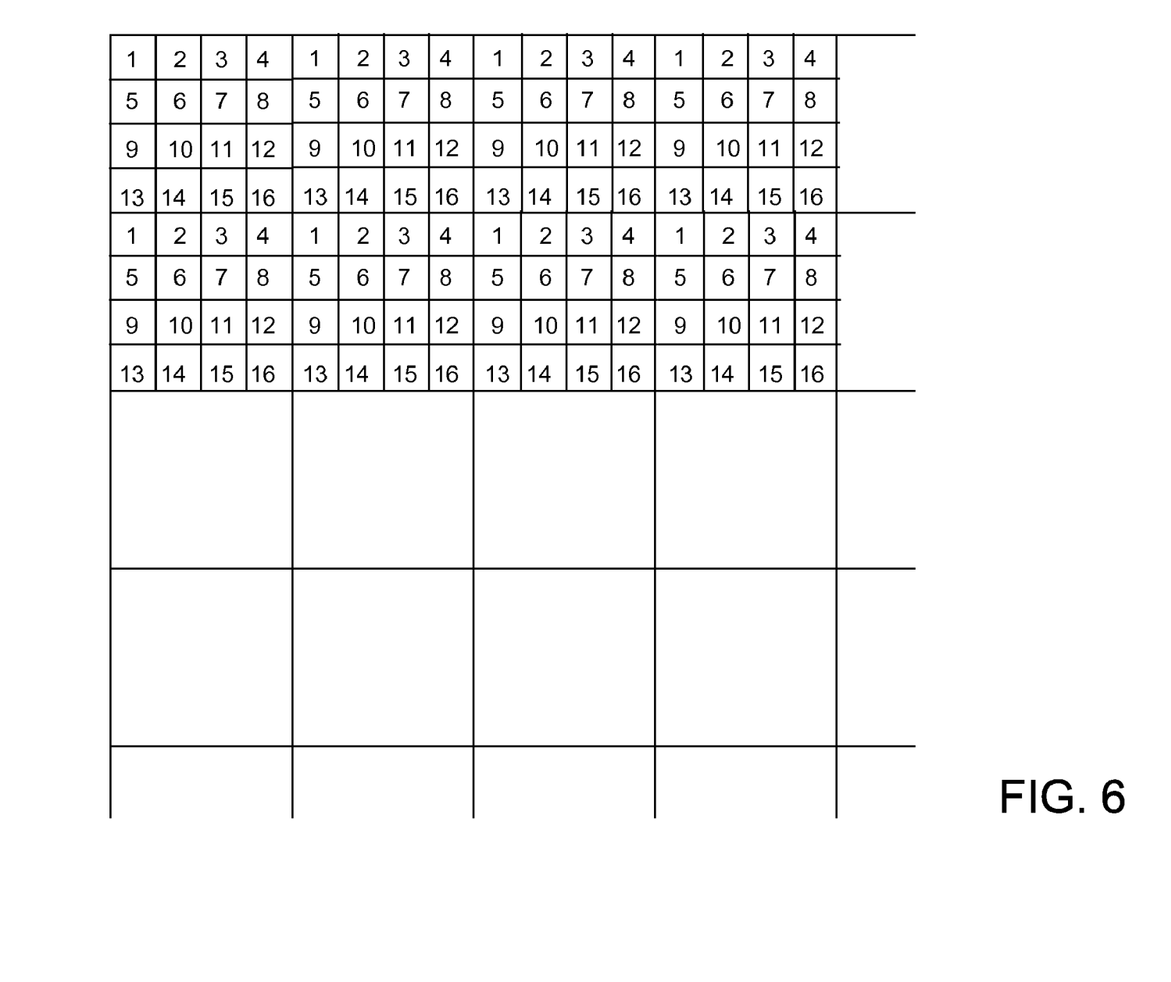
FIG. 6 shows an example of a filter matrix pattern.

FIG. 6 shows an example of a filter matrix pattern. In this example, a 4×4 array forms one super-pixel. Sub-pixels correspond to filter matrix elements number 1 through 16. The 16-element filter matrix pattern is repeated across the image array. A regular packed pattern of super-pixels fills the image array area. Light passing through one micro lens fills one super-pixel area.

Figure 7:
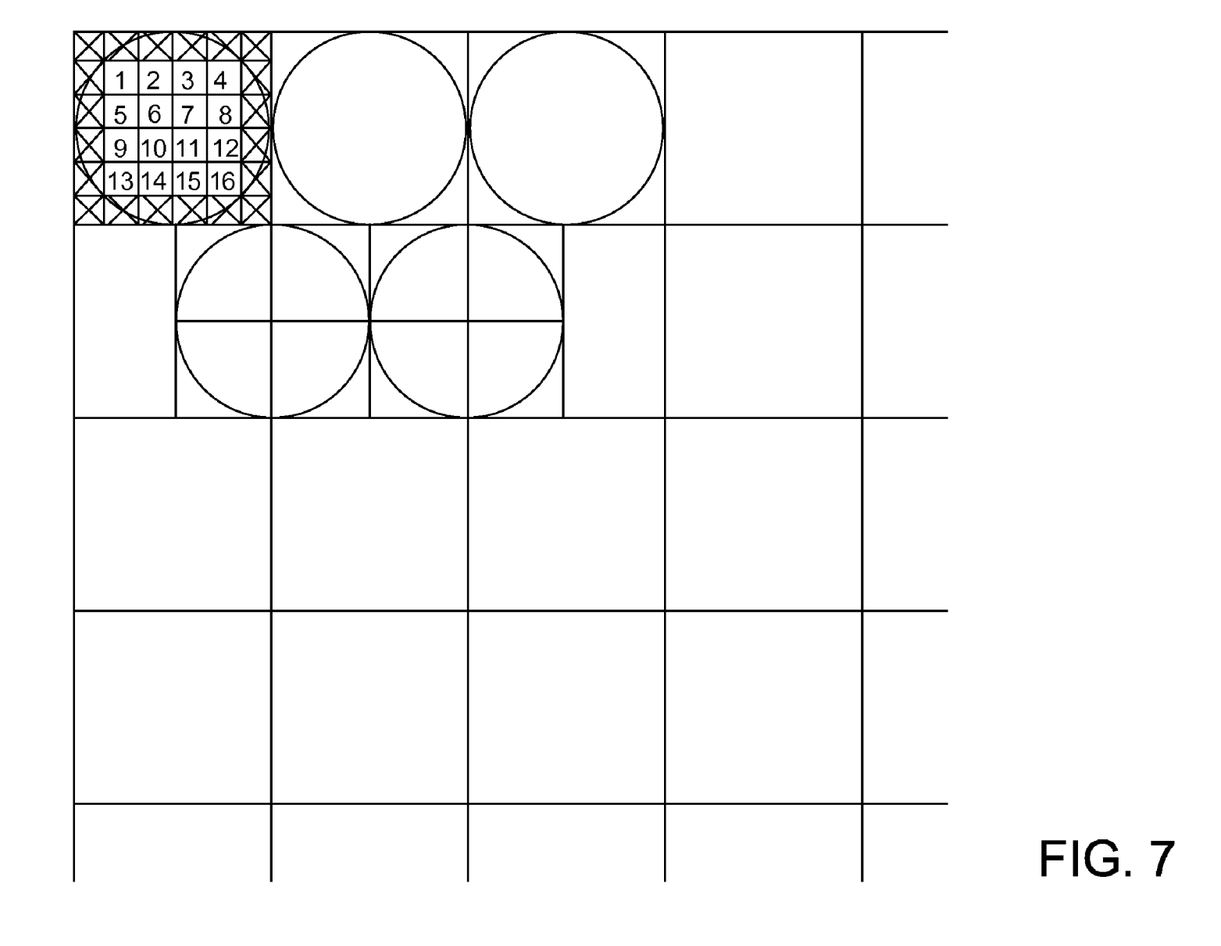
FIG. 7 shows an example of an alternate filter matrix pattern to increase isolation between super-pixels.

FIG. 7 shows an alternative filter matrix pattern with unused pixel positions between lenses. One or more pixels between each super-pixel can be sacrificed to insure that no light from adjacent super-pixels is received. Additionally, this filter matrix pattern can be used with a circular or alternately shaped limiting aperture or a limiting aperture that is created by the finite size of the objective lens itself. The 16 colors of the filter matrix corresponding to 16 pixels on the image array are circumscribed by the circular region. A perimeter around the active filter matrix area is not used because a full pixel is not covered by the projected image. Alternatively, other pixels arrangements can be used to approximate an area that more closely corresponds to the projected image area.

The boundary between lenses may have excessive optical impairments, thus areas of unused pixels can be assigned to these dark areas. The filter matrix defines which pixels are used. The required size of the detector array increases for a given resolution due to unused pixels, or reduces the resolution available for a given size array. The benefit gained is improved illumination uniformity across the super-pixel, even though detector real estate is not fully used with this alternative filter matrix pattern.

Color Separator

Figure 8:
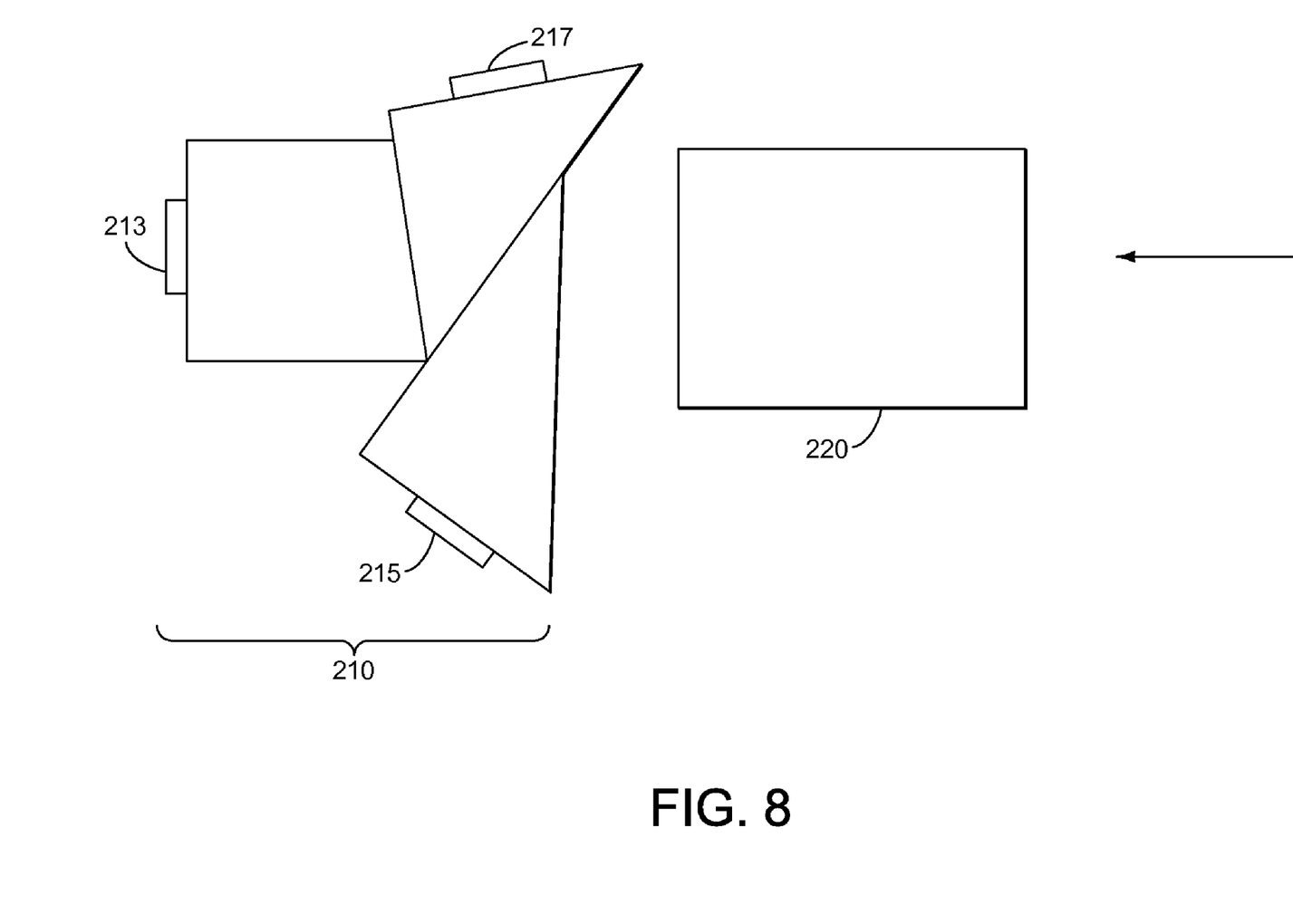
FIG. 8 shows a color separating prism assembly directing light sub-bands onto three imagers.

FIG. 8 shows color separator prism 210 receiving an image from objective lens 220. Color separator 210 splits the incident image into three sub-bands. Imagers 213, 215, and 217 are positioned on the output face of each prism and further resolve each sub-band into narrower frequency bands. Each imager 213, 215, and 217 comprises a micro-lens array, color filter matrix and imaging detector array, each forming a hyperspectral imager.

Figure 9:
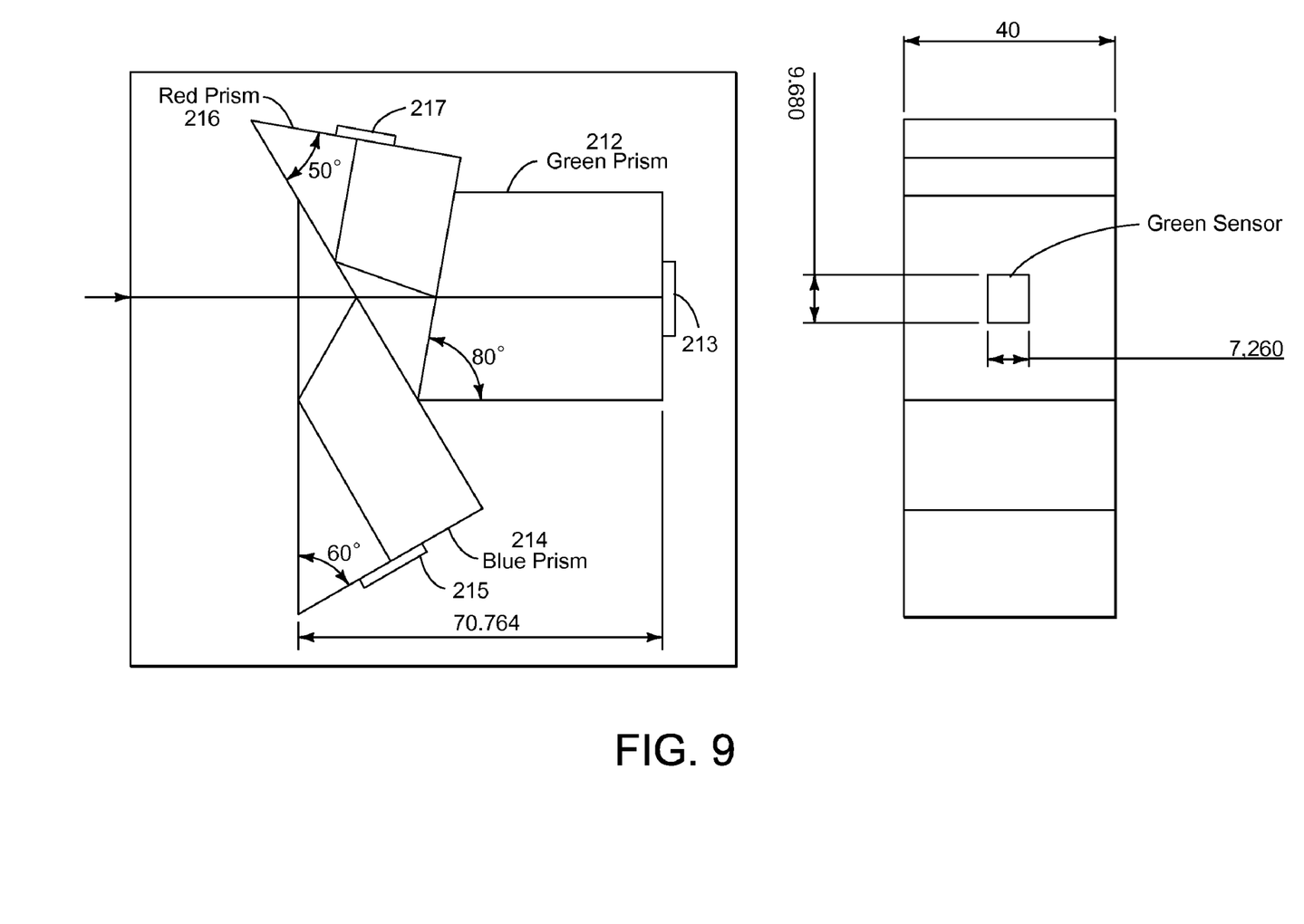
FIG. 9 shows details of a color separating prism assembly suitable for use with the present invention.

FIG. 9 shows color separator prism 210 comprising green prism 212, blue prism 214, and red prism 216. Two dichroic filters located at the prism interfaces act as band splitters. One band-splitting filter is located between blue prism 214 and red prism 216. The other band-splitting filter is located between red prism 216 and green prism 212. The dichroic filters can be deposited directly on the surface of the prisms. Red/Green/Blue are representative colors, the actual wavelengths of each sub-band can be any wavelength including above and below the visible spectrum used in this example. The technique of using color-separating prisms can be applied to 2 bands or more. Using three imaging arrays with a filter matrix array covering 16 separate narrow bands, 48 wavelength bands in total can be covered.

Figure 10:
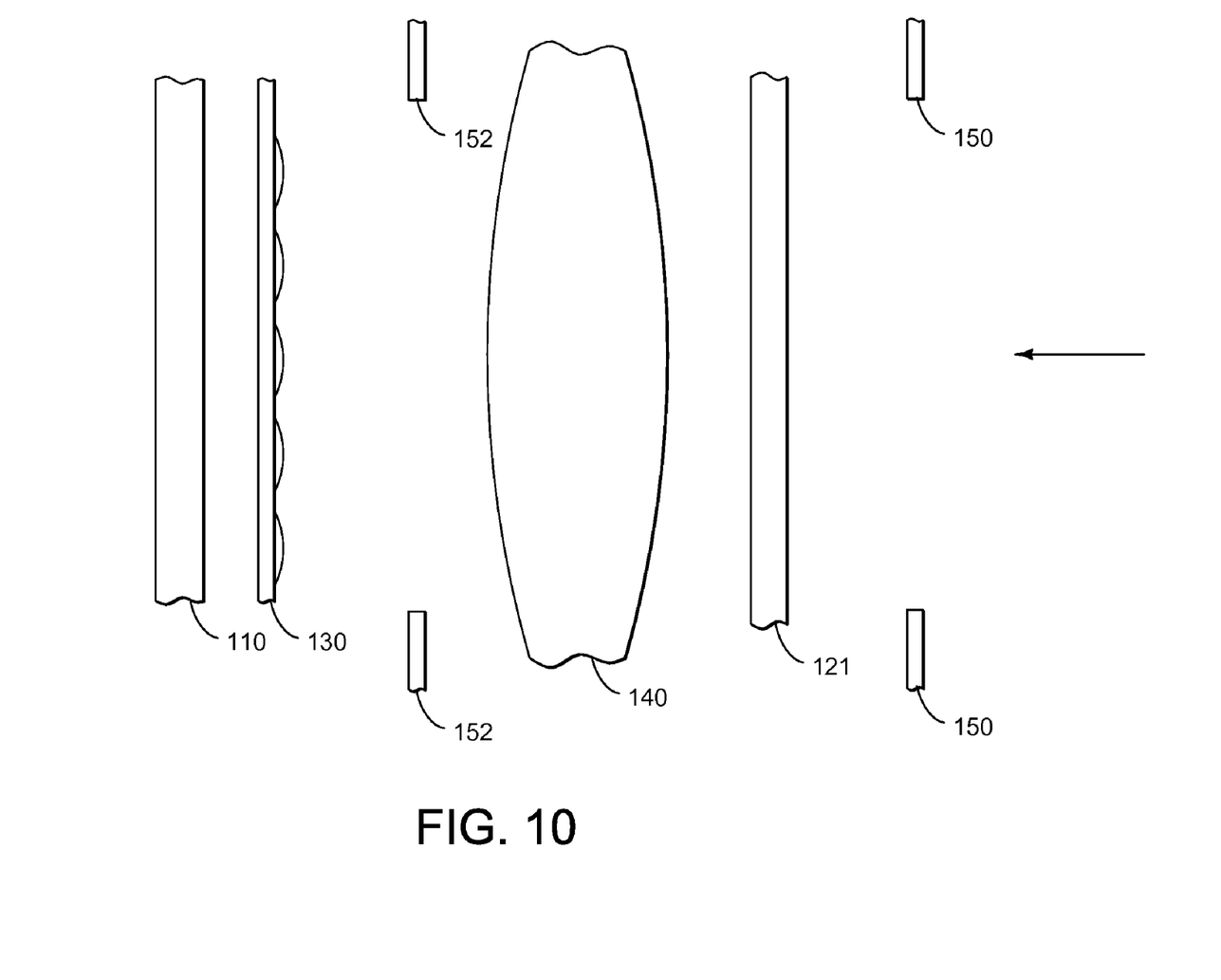
FIG. 10 shows the side view of the components of an alternate embodiment of the hyperspectral imager with a spectral filter at the objective lens.

FIG. 10 shows the side view of the components of an alternate embodiment of the hyperspectral imager. In this embodiment, the color filter function is performed at the objective lens. The color filter array 121 is shown positioned at the entrance pupil of the objective lens 140. The filter array 121 may alternatively be placed on the other side of the objective lens 140, for example prior to the exit aperture 152, by strategic placement of the optical pupil in the lens design process. One implementation uses a single 4×4 filter array. MLA 130, comprising many lenslets, one for each super-pixel group, re-images this single filter matrix onto the groups of pixels on the detector array 110, with each group comprising 4×4 pixels. An advantage of this technique is that the filter matrix is easier to produce—each filter in the 4×4 matrix is several millimeters on a side compared to the several micrometer size of each filter of the on-FPA filter matrix. Additionally, the larger filter matrix is easier to change at an accessible point in the optical path. A disadvantage is that the matrix must be matched to the fore-optic.

Figure 11:
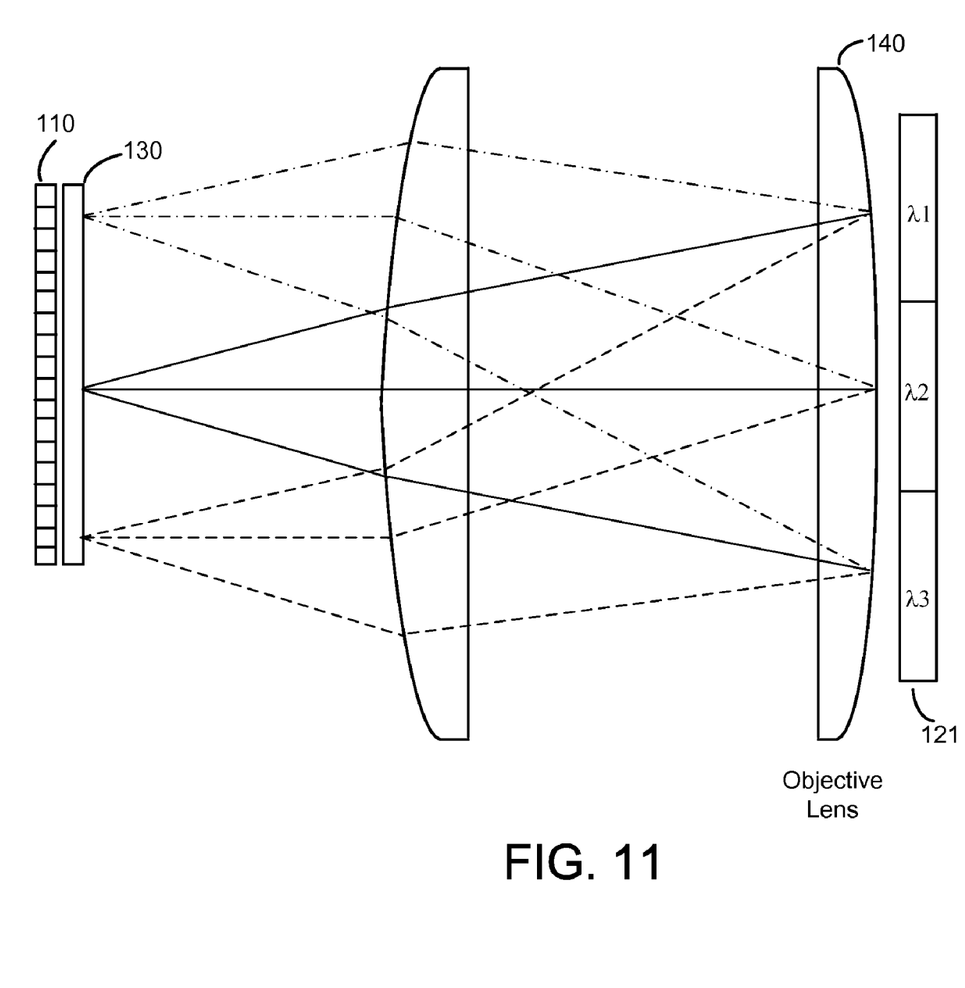
FIG. 11 shows ray tracing of the optical path for three different wavelengths with the spectral filter at the objective lens.

FIG. 11 shows ray tracing of the optical path for three different wavelengths with the spectral filter 121 at the objective lens 140. In this cross sectional view, three wavelengths are show for filter array 121, however the array can comprise many different wavelengths arranged in a two-dimensional square or rectangular array or other configuration. Note that the micro-lens array 130 lenslet images are not of the macroscopic scene imaged by the objective lens. Rather, it is a finite-conjugate image of the spectral filter array located at the entrance pupil. The brightness of the spectral filter elements within each lenslet image group, a super-pixel on detector array 110, on the focal plane depends on the spectral radiance of the scene at the particular spatial angle as viewed by the pixel group and by the spectral bandpass characteristic of the filters used in the array.

The preferred embodiment of the design is an image-telecentric lens as the image-forming objective for the system. Such a lens is designed with the exit pupil placed at infinity, so that the chief rays emerge parallel from the last optical element of the lens, and thus at normal incidence to the image plane. FIG. 11 illustrates a simple telecentric lens configuration for this type of lens with two lens elements.

Figure 12:
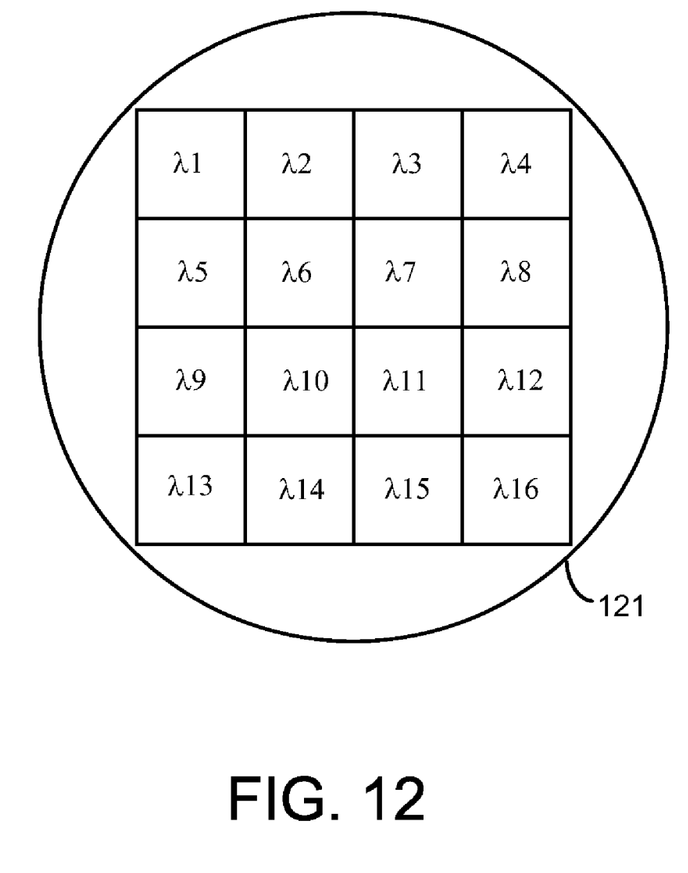
FIG. 12 shows a filter matrix for use at the entrance pupil of the objective lens.

FIG. 12 shows a filter matrix 121 for use at the entrance pupil of the objective lens that results in projecting a replicated image of the filter matrix onto each superpixel across the focal plane. The layout and shape of the filters used in the design must match the layout and shape of the imaging focal plane array (FPA). If the imaging pixels are square and arranged in a rectilinear pattern then the spectral filter array must also have square elements arranged in a rectilinear pattern. If non-square pixels comprise the imaging array then the shape of the filter elements must have the same aspect ratio as the pixels.

Data Processing

The HSI described here can generate large amounts of data. A technique for acquisition and processing of data at real time rates of 30 cubes per second is described in Dombrowski et al., U.S. Pat. No. 5,949,074 "Imaging Spectroradiometer", incorporated herein by reference. The techniques for reading the electronic signals from CMOS detector arrays are well known. Generally, digital and analog circuitry interfaces with the detector array to control the readout of rows and columns of image induced signal at each pixel. Preferably, an analog to digital converter digitizes the analog signal from the detector and further storage and processing of the image data is done digitally.

The invention claimed is:

1. A hyperspectral imager comprising:
   an objective lens for producing a focused image at a focal plane;
   an array of spectral filters placed at the entrance pupil of the objective lens, each spectral filter element passing a band of light;
   a detector array comprising a plurality of multiband detectors, each multiband detector comprising a plurality of detectors;
   a micro-lens array comprising a plurality of micro-lenses, positioned between the objective lens and the detector array, each micro-lens of the micro-lens array positioned approximately at the focal plane to produce an image for one multiband detector;
   wherein all detectors of one multiband detector receive substantially the same image and each detector of one multiband detector receives light from one element of the array of spectral filters.

2. The hyperspectral imager of claim 1 wherein the objective lens is telecentric.

3. The hyperspectral imager of claim 1 further comprising a limiting aperture positioned at the objective lens that defines the image shape projected onto a multiband detector.

4. The hyperspectral imager of claim 2 further comprising a limiting aperture positioned at the objective lens that defines the image shape projected onto a multiband detector.

5. The hyperspectral imager of claim 2 comprising a limiting aperture positioned between the objective lens and the micro-lens array that defines the image shape projected onto a multiband detector.

* * * * *